United States Patent [19]

Warriner

[11] Patent Number: Plant 5,978

[45] Date of Patent: May 12, 1987

[54] ROSE PLANT JACRO

[75] Inventor: William A. Warriner, Tustin, Calif.

[73] Assignee: Jackson & Perkins Company, Medford, Oreg.

[21] Appl. No.: 771,850

[22] Filed: Sep. 3, 1985

[51] Int. Cl.[4] ..... A01H 5/00

[52] U.S. Cl. ..... Plt./28

[58] Field of Search ..... Plt./28–29

*Primary Examiner*—Robert E. Bagwill

*Attorney, Agent, or Firm*—Manford R. Haxton

[57] ABSTRACT

A floribunda rose variety having outstanding flower production because of its vigorous continual growth, a velvet red flower color with petals averaging 24–27 per flower and unusual purplish filament color.

1 Drawing Figure

This present invention relates to a new and distinct variety of rose plant of the floribunda class which was originated by crossing an unnamed variety with the Gabriella, U.S. Plant Pat. No. 4,452.

The primary objective of this breeding was to produce a new rose variety of the floribunda class exhibiting a rich red flower color and adaptable to greenhouse cut flower production. This objective was substantially achieved along with other desirable improvements as evidenced by the following unique combination of characteristics which are outstanding in the new variety and which distinguish it from its parents as well as from all other varieties of which I am aware:

1. Rich velvet red color;
2. Outstanding production;
3. Vigorous continual growth;
4. Purplish filament color; and
5. Petal number between 24–27.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—Unnamed variety.

*Pollen parent.*—Gabriella, U.S. Plant Pat. No. 4,452.

Classification:

*Botanical.*—Rosa hybrid.

*Commercial.*—Floribunda.

FLOWER

Observations made from specimens grown in a greenhouse at Irvine, Calif. in June.

Blooming habit: Continuous.

Bud:

*Size.*—1¼" when petals start to unfurl.

*Form.*—Long, blunt top.

*Color.*—When sepals first divide, rich, velvet red (Red Group 44A); when half blown, upper side of petals Red Group 44A to 44B; lower side of petals Red Group 44A to 44B.

*Sepals.*—Color: Green 138B. Three appendaged sepals lightly appendaged with occasional foliaceous sepals. Two unappendaged sepals hairy edge.

*Receptacle.*—Color: Green Group 138B. Shape: Funnel. Size: Small, slender. Surface: Smooth.

*Peduncle.*—Length: Medium. Surface: Glandular. Color: Medium green. Strength: Stiff.

*Opening.*—Petals open normally with slight quilling.

Open bloom:

*Size.*—Medium. Average open size 3".

*Borne.*—Singly, to several together.

*Stems.*—Medium, strong.

*Form.*—When first open, cupped, high center. Permanence: Flattens, slightly quill fashion.

*Petalage.*—Number of petals under normal conditions: 24–27.

*Color.*—Center of flower: Upper side of petals, Red Group 44A to 44B; reverse side of petals, Red Group 44A to 44B. Base of petals, small white area. Major color: Red 44A to 44B.

*Variegations.*—Occasional white vegetative streak in center of outer petal.

*Discoloration.*—General tonality at end of first day: No change. Third day: Near Red 45B to 46C.

*Fragrance.*—Slight.

Petals:

*Texture.*—Thick.

*Shape.*—Round.

*Form.*—Tips slightly recurved, outer petal edges slightly quilled.

*Arrangement.*—Imbricated.

*Persistence.*—Drop off cleanly.

*Lastingness.*—On the plant, long. As cut flower, long.

Reproductive parts:

*Anthers.*—Medium. Color: Yellow, Yellow Orange Group 22B. Arrangement: Regular around styles.

*Filaments.*—Color: Purplish.

*Pollen.*—Lemon Yellow.

*Styles.*—Color: Red.

*Stigmas.*—Color; White.

PLANT

Form: Bush.

Growth: Vigorous.

Foliage:

*Number of leaflets on normal mid-stem leaves.*—5 or 7.

*Size.*—Medium.

*Quantity.*—Normal.

*Color.*—New foliage: Light Green 138B with overtone of reddish pigment. Old foliage: Dark Green 139A.

Leaflets:

*Shape.*—Elliptic pointed.

*Texture.*—Leathery.

*Edge.*—Serrated.

*Serration.*—Single, small.

*Petiole.*—Rachis: Color: Green. Underside: Smooth, with a few prickles.

*Stipules.*—Short, bearded.

*Disease resistance.*—Normally resistant to mildew, under normal growing conditions at Irvine, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Hooked downward.

*Color when young.*—Red.

Small prickles:

*Quantity.*—On main stalks, none. On laterals, few.

*Color.*—Green.

I claim:

1. A new and distinct variety of rose plant of the foribunda class, substantially as herein shown and described, characterized particularly as to novelty by the unique combination of its outstanding flower production because of its vigorous continual growth, a velvet red flower color with petals averaging 24–27 per flower and its unusual purplish filament color.

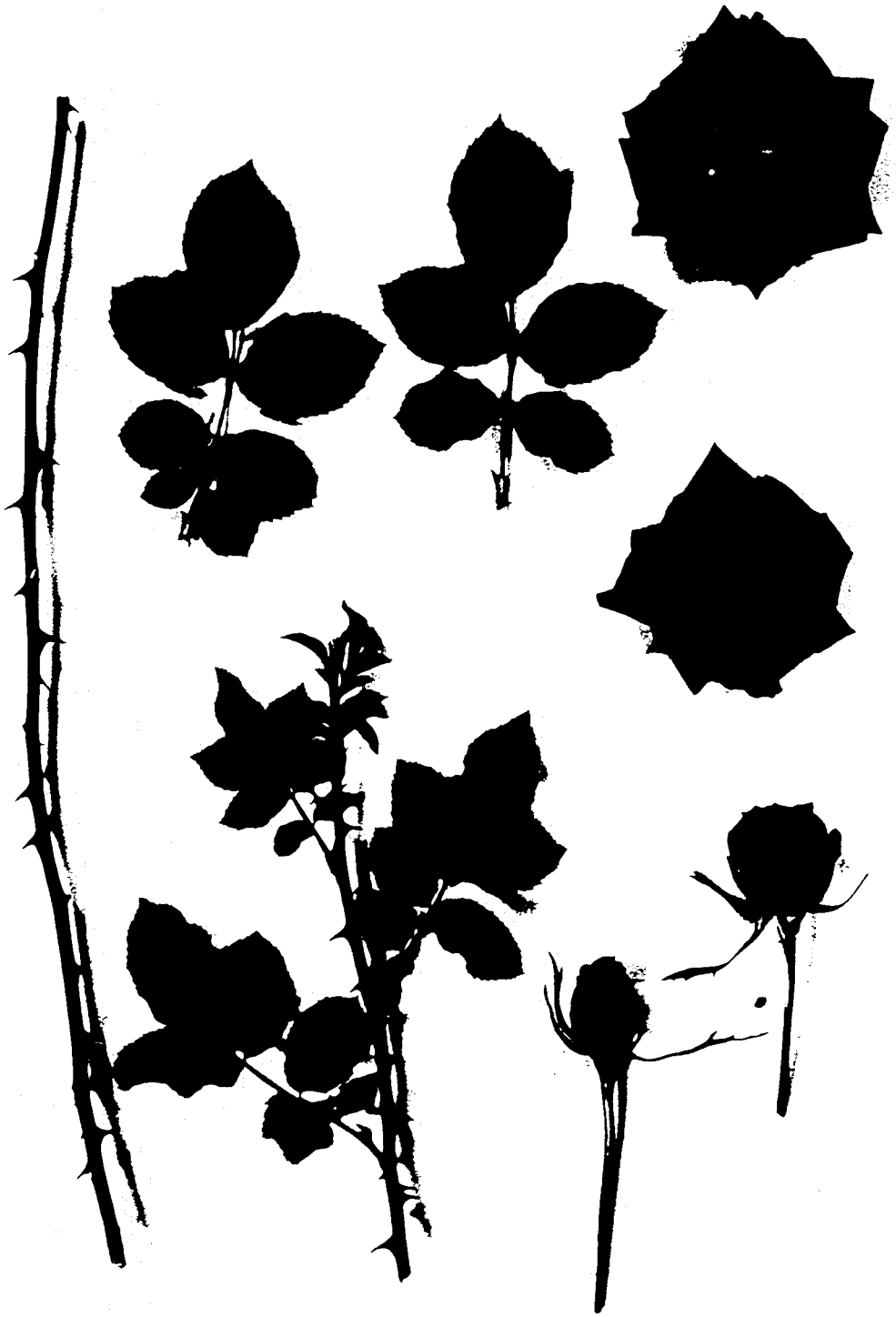

* * * * *